(12) United States Patent
Mirarchi

(10) Patent No.: US 11,164,129 B2
(45) Date of Patent: Nov. 2, 2021

(54) ADVANCE MEDICAL DIRECTIVES AND END-OF-LIFE ORDERS WITH SCRIPTED VIDEO

(71) Applicant: Ferdinando Mirarchi, Erie, PA (US)

(72) Inventor: Ferdinando Mirarchi, Erie, PA (US)

( * ) Notice: Subject to any disclaimer, the term of this patent is extended or adjusted under 35 U.S.C. 154(b) by 24 days.

(21) Appl. No.: 16/268,163

(22) Filed: Feb. 5, 2019

(65) Prior Publication Data

US 2019/0244685 A1    Aug. 8, 2019

Related U.S. Application Data

(60) Provisional application No. 62/628,183, filed on Feb. 8, 2018.

(51) Int. Cl.

| | |
|---|---|
| G06Q 10/06 | (2012.01) |
| G16H 10/20 | (2018.01) |
| G16H 10/60 | (2018.01) |
| H04N 5/765 | (2006.01) |
| G06F 40/30 | (2020.01) |

(52) U.S. Cl.
CPC ....... G06Q 10/06316 (2013.01); G06F 40/30 (2020.01); G16H 10/20 (2018.01); G16H 10/60 (2018.01); H04N 5/765 (2013.01)

(58) Field of Classification Search
CPC ... G06Q 10/06316; G16H 10/60; H04N 5/765
See application file for complete search history.

(56) References Cited

U.S. PATENT DOCUMENTS

| | | | | |
|---|---|---|---|---|
| 8,306,830 B1* | 11/2012 | Renuart | ................. | G16H 40/20 |
| | | | | 705/2 |
| 10,296,716 B1* | 5/2019 | Skocic | .................... | G06F 16/13 |
| 2003/0040939 A1* | 2/2003 | Tritch | .................... | G16H 10/20 |
| | | | | 705/2 |
| 2005/0177400 A1* | 8/2005 | Rosenfeld | ............ | A61B 5/4094 |
| | | | | 705/3 |
| 2008/0027752 A1* | 1/2008 | Phan | ...................... | G16H 10/60 |
| | | | | 705/2 |
| 2008/0228524 A1* | 9/2008 | Brown | ................... | G16H 10/60 |
| | | | | 705/3 |
| 2012/0310670 A1* | 12/2012 | Pruitt | ..................... | G16H 10/20 |
| | | | | 705/3 |
| 2014/0249850 A1* | 9/2014 | Woodson | ............... | G16H 20/00 |
| | | | | 705/3 |
| 2015/0242812 A1* | 8/2015 | Nelson | .................. | G16H 40/67 |
| | | | | 705/311 |

(Continued)

*Primary Examiner* — Michael Tomaszewski
*Assistant Examiner* — Jay M. Patel
(74) *Attorney, Agent, or Firm* — Jonathan M. D'Silva; MMI Intellectual Property

(57) ABSTRACT

A system and method for documenting medical directives of a patient is presented. This comprises identifying the possible paths required to document the medical directives of the patient. For each path, identifying missing information and required user input to complete the path. Then generating a workflow process for a selected path that comprises collection of missing information, manipulation of user provided data, and identification and generation of required documentation necessary for the completion of the selected path. The workflow process is executed for the selected path and a patient specific token is created to memorialize the execution of the workflow process.

8 Claims, 2 Drawing Sheets

(56) References Cited

U.S. PATENT DOCUMENTS

| | | | |
|---|---|---|---|
| 2017/0280065 A1* | 9/2017 | Cohen | H04N 21/4305 |
| 2017/0293988 A1* | 10/2017 | Goyal | G16H 10/20 |
| 2019/0236736 A1* | 8/2019 | Malik | G16H 10/60 |

* cited by examiner

ADVANCE MEDICAL DIRECTIVES AND END-OF-LIFE ORDERS WITH SCRIPTED VIDEO

BACKGROUND

Individuals are entitled to record medical directives and end-of-life orders and have those instructions honored when they are receiving emergency health care and in general to have their medical directives followed. Such medical directives can sometimes be ignored or overlooked especially in the heat of moment when emergency health services are being provided. What is provided is a more efficient system and method for allowing individuals to create clear instructions to end-of-life and emergency caregivers and to provide a system to allow end-of-life and emergency caregivers to quickly access such instructions.

SUMMARY

What is presented is a system and method for documenting the medical directives of a patient. The medical directives of a patient comprise advanced care planning, resuscitation choices, end-of-life wishes, and consent for treatment. The system and method identify the possible paths required to document the medical directives of the patient. In some embodiments, the user is provided with documentation and education for each possible path. For each path, missing information and required user input to complete the path is identified. A workflow process is generated for a selected path that comprises collection of missing information, manipulation of user provided data, and identification and generation of required documentation necessary for the completion of the selected path. The workflow process for the selected path is executed and memorialized by creating a patient specific token. The token is one of an identification card, a necklace, a bracelet, jewelry, a software application, and a device.

In some embodiments the workflow process further comprises generating a script that is specific to the selected path. The workflow process may include generating a recording of the patient reading the script. The recording may be video, audio, or both. A final recording that combines the patient reading from the script with a timed scrolled visual match up of the script following the patient's recitation of the script could also be created.

Those skilled in the art will realize that this invention is capable of embodiments that are different from those shown and that details of the devices and methods can be changed in various manners without departing from the scope of this invention.

Accordingly, the drawings and descriptions are to be regarded as including such equivalent embodiments as do not depart from the spirit and scope of this invention.

BRIEF DESCRIPTION OF DRAWINGS

For a more complete understanding and appreciation of this invention, and its many advantages, reference will be made to the following detailed description taken in conjunction with the accompanying drawings.

DETAILED DESCRIPTION

Figure 1:
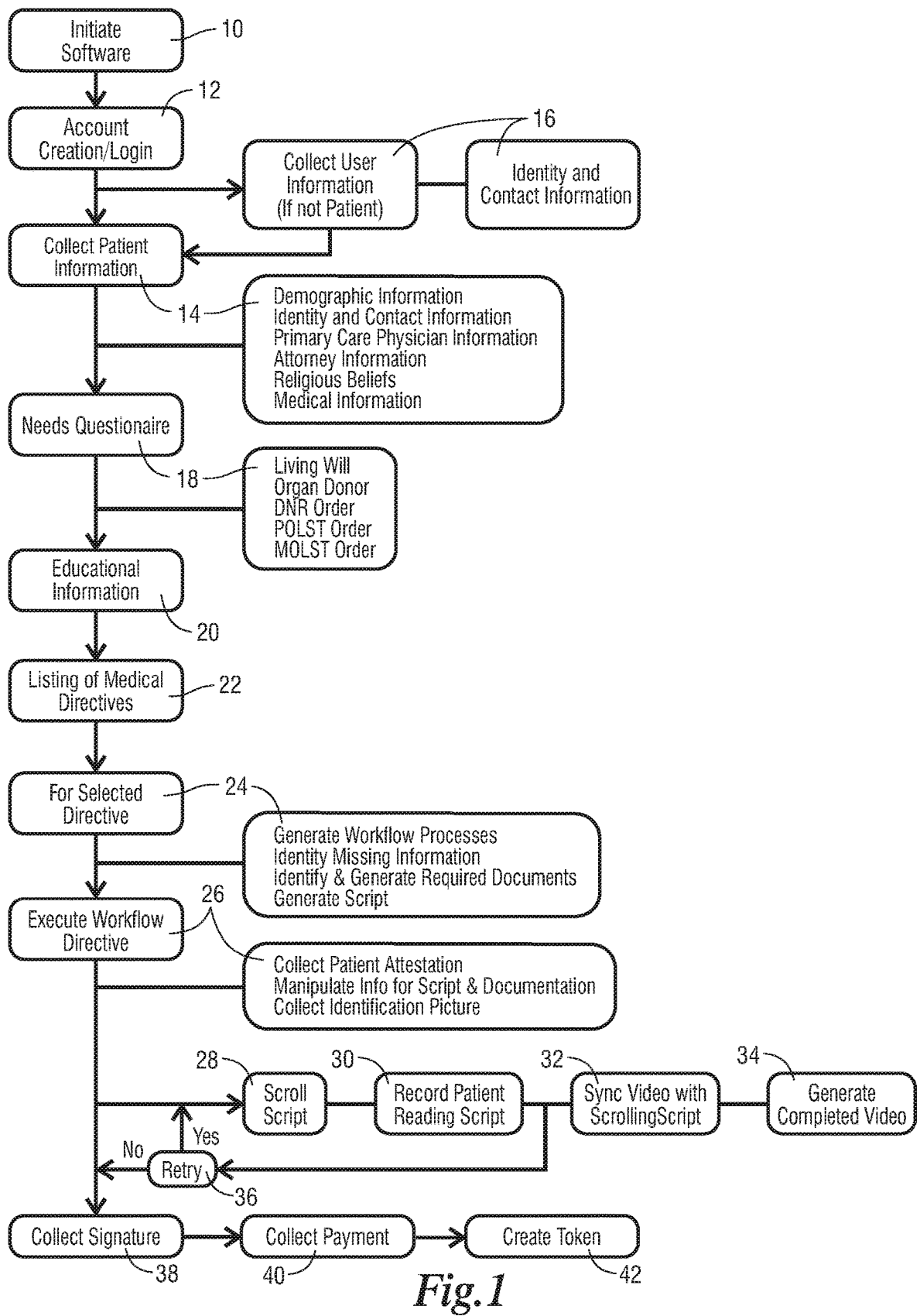
FIG. 1 is a flow chart showing how medical directives of a patient are documented.

Referring to the drawings, variations of corresponding parts in form or function that are depicted in the figures are described. It will be understood that variations in the embodiments can generally be interchanged without deviating from the invention.

In end-of-life (EOL) care individuals attempt to address in advance how they would want to be treated at EOL and emergency situations. Now, advance directives, or advance care planning documents, most commonly living wills, do not resuscitate orders (DNR), and documents like physician orders for life-sustaining treatment (POLST) and medical orders for life-sustaining treatment (MOLST) are tools utilized for advance care and EOL planning. Until recently they have not appeared to be a patient safety risk. These documents are well meaning and well-intended; however, they have in fact led to unintended consequences as reported on multiple occasions in the press.

These documents are typically legal documents filled with legal jargon that must then be interpreted by health care professionals who have little to no training in what the documents say, let alone what these documents are, and even if they did, these documents aren't always readily available to the health care professional until after treatment has been provided. In many cases, studies have shown that practitioners often make assumptions about the content of such documents without reading them.

The system and method presented herein documents the medical directives of a patient to allow for easier access to such documents and using language designed to be understood by the health care provider. The system combines a software platform that leads to the creation of a token that the patient can have on their person. The software platform would be available as downloadable application on a computing device such as a smartphone or a personal computer that is connected to a video camera or some other system that can record voice and/or video.

As shown in the flowchart of FIG. 1, the system is designed to operate on a computing device to create the documentation required to memorialize the medical directives of patients. Medical directives comprise advanced care planning, resuscitation choices, EOL wishes, consent for treatment, and other types of documentation for which a memorialization of treatment choices of a patient need to be recorded. The system is intended to safely and effectively enable the voice of the patient through completion and utilization of advance care planning documents, medical, surgical, pediatric, and psychiatric care plans as well as virtual medical informational alerting and guidance. This also can pertain to care management and procedural consent related to surgical procedures or procedures requiring informed consent.

The patient may go through the process described herein by themselves, or they may do so with the assistance of a third party like a loved one, caregiver, trained medical professional, or a legal professional. In addition, the system may be provided with a virtual assistant to provide assistance and/or guidance as needed or may include access to on-line or telephonic assistance from a service provider or technical assistant. Whether or not the patient is creating the documentation by themselves or with assistance, we herein refer to the person interacting with the software as a "user" working on behalf of the "patient" for whom the documentation is being generated. If the process is conducted with the assistance of a third party health care provider, it could be accompanied by informational patient interviews to determine individualized and personal requirements. Referring to FIG. 1, the software is initiated 10 and prompts the user to log in 12 with their user credentials in the case of a returning user or to create a new account in the case of a new user.

In instances where the system is used to collect consent for treatment memorialization, it is possible that the user is the health care provider that will be performing the treatment. This system will allow memorialization of the patient's choice for treatment to be recorded as described herein and such memorialization can be kept as part of the patient's medical records and incorporated as part of the health care provider's due diligence.

The system begins with collecting some basic identification, contact, and demographic information from the patient 14, including but not limited to name, age, gender, mailing address, primary care physician, legal counsel, medical information, and religious beliefs. Collection of medical information allows information to be passed on to medical providers that can be displayed or carried by patients to allow for their safe and effective treatment in a medical crisis or resuscitation scenario.

If the user is not the patient 16, the user's information is also collected and recorded as part of the due diligence of the process to identify the user as the patient's healthcare agent that is authorized to act on the patient's behalf. This includes the name and contact information of the user.

The user is presented with a needs questionnaire 18 for identifying the required medical directives of the patient. The questionnaire could cover a variety of topics including living wills, organ donation, DNRs, POLSTs, questions about how and whether the patient wishes to be treated if they are critically ill, or, in the case of obtaining consents for treatment, questions about the procedure sought. Based on the answers to these questions, a variety of educational content 20 will be presented such as written material, audio recordings, videos, or other material related to the patient's needs. In the case of consents for treatment, the system allows for documenting a patient/clinician discussion with the ability to accurately inform the next healthcare provider, with high degrees of accuracy, the informed and shared decision making that occurred between the primary physician and the patient previously.

The possible medical directive paths will be identified and presented to the patient 22. For each possible path, a summary of what each path entails as well as offer additional explanation or clarification for the implications of each path will be provided. For each selected path 24, workflow processes and documentation are generated that includes collection of missing information, manipulation of user provided data necessary for the completion of the path, and identification and generation of required documentation necessary for the completion of the selected path. A script will also be generated that will be read by the patient to record their selection of medical directive. The scripts are a combination of medical and legal terms to reflect treatment decisions when critically ill as well as when at EOL. In general, depending on the patient's requirements, the script will be tailored to provide accurate medical direction to caregivers while adhering to the legal requirements for such instructions. This addresses the issue where such documents in the prior art are written in legalese without adequate medical definition of what the patient intends. These legal requirements will depend on the jurisdiction that the patient resides.

On executing the workflow process for the selected path 26, the patient will be prompted to acknowledge and attest that they understand the choice they are making. If necessary, the patient could be asked to complete a quiz to show their comprehension of their choice. The patient provided information is manipulated to complete the script for the patient to read and complete all documentation required to memorialize the patient's choice of medical directive. A photograph of the patient could also be collected for identification purposes.

At this time, the patient is prompted to get ready to read and record their statement. When prompted to do so, the script will be scrolled before the patient 28 and the patient recorded with a video camera as they read the script 30. This may be an audio recording only, but a video recording is preferred as it would have some visual indication of the patient's state of mind that may not come across in an audio-only recording. The patient is given the option of watching the video (or listening to the audio) and re-recording it if necessary 36.

The recording is then synced with a rolling display of the script as it is being read by the patient 32. This finally generated recording 34 would allow anyone watching the video (or listening to the audio) to follow along with the patient and reduce any misunderstanding of what the patient may be saying. This would be especially useful for patients who have heavy accents or caregivers who do not speak the same language as a first language as the patient. The recording may be edited and reviewed before it is finalized and there could be other quality control checks done before the video is accessible.

Once all the documentation has been completed, signatures of the patient and the user are collected 38 and payment is processed 40. A patient specific token is then created 42 that memorializes the execution of the workflow process. The token allows anyone with access to it to connect to the patient's memorialization of their selected medical directive. The token enables the safe, timely, and effective storage, retrieval, and utilization of such documents to help to minimize or eliminate medical errors.

The token can could be an identification card, a necklace, a bracelet, jewelry, a software application, a smart watch, a device, or some other system. The token could be embedded in a necklace, a bracelet, jewelry, or other ornamentation onto which basic information to link to a patient specific webpage and access the patient's documentation and recordings of their medical directives. The token could also be included as an application on a smartphone which would direct anyone to the patient's documentation and recording. Or it could be another standalone device that serves the same purpose.

Figure 2:
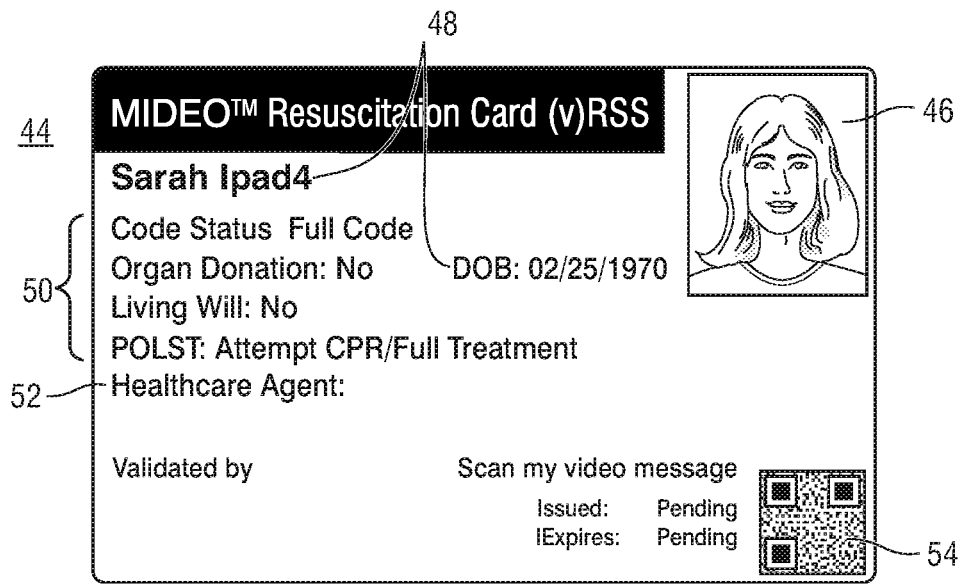
FIG. 2 shows an example of a token that is an identification card that memorializes the execution of a selected workflow process to document the medical directives of a patient.

If the token is an identification card 44 as shown in FIG. 2, the patient could carry it with their driver's license or health insurance cards. The identification card could include an identification photograph of the patient 46, listing basic identification information 48, such as name, date of birth, possibly social security information, and other medical information including summaries of the patient's chosen medical directives 50, such as medical code status designation with or without Medical Alerting information (such as airway concerns), organ donation declaration, and directives such as living wills, DNR, or POLST/POLST like information when available. This also informs as to who holds or where these documents can be obtained. If there is health care agent or emergency contact person available, their information could also be listed 52. The card could also be provided with a QR code 54 or some other system that provides a link to a patient specific webpage that would provide additional details as to the specific medical directives of the patient. This will allow medical providers to scan the code to access the database where the patient's clarification instructions can then be viewed by the medical provider to affect care in real time. This could also include the finally generated recording as created earlier as well as any documentation necessary to memorialize the patient's medical directives. The QR codes may or may not be encrypted with password technology. The database will require a password to enter and access the patient's informational statement.

The back of the identification cards could be customized with a company logo (healthcare insurer, hospital, law office, etc.). The card could bear a physician signature's, the patient signature, and/or a witness signature. The identification cards can act as a medical order if they are dated and signed by a physician as well as the patient. The patient's contact information could also be included in the event the card is lost. A magnetic strip could also be included to provide retrievable information.

When the patient is in a medical crisis where they cannot speak for themselves, medical providers are trained to look for driver's license, medical alert bracelets/medallions, and/or insurance information. When they come across a token such as an identification card or other described above, they would review the medical information to act in accordance with the patient's wishes. If there is any doubt on the part of the medical provider, the medical provider can utilize any smartphone, equipped with a QR card reader, simply scan the code and within seconds have the video clarification statement by the patient.

If the patient is conscious and able to respond to questions, the patient simply hands the token to the appropriate person. The intake person or any medical provider would then follow the medical directives as necessary.

The system could incorporate smart watch technology that detects a patient's pulse. When the pulse disappears or the patient activates a SOS trigger, the patient's location will be determined by the watch. Emergency services would be contacted and given the location of the patient. When Emergency Medical Service providers arrive, they would need to press the reset button on the smart watch. At that point the system would stand down and begin to play the patient's recorded medical directive statement.

The system and method disclosed herein advances the development of patient-to-clinician video to accurately and safely guide care decisions when a patient is critically ill or at EOL situations. This provides the ability to be a hand off communication tool between patient-to-clinician as well as clinician-to-clinician. Another advantage of the system presented herein is that the recordings are particularly useful for patients who are visually or hearing impaired. Having a pre-recorded message means that health care providers can hear their wishes even if they cannot communicate with the patient.

The system can also be used for surgery pre-operative DNR order clarifications to address the inappropriate practice to reverse DNR orders prior to an operative procedure. The American Anesthesia Society states that there are at least 15 percent of patients who undergo surgical procedures for palliative reasons who's wishes are being disregarded and disrespected.

Figure 3:
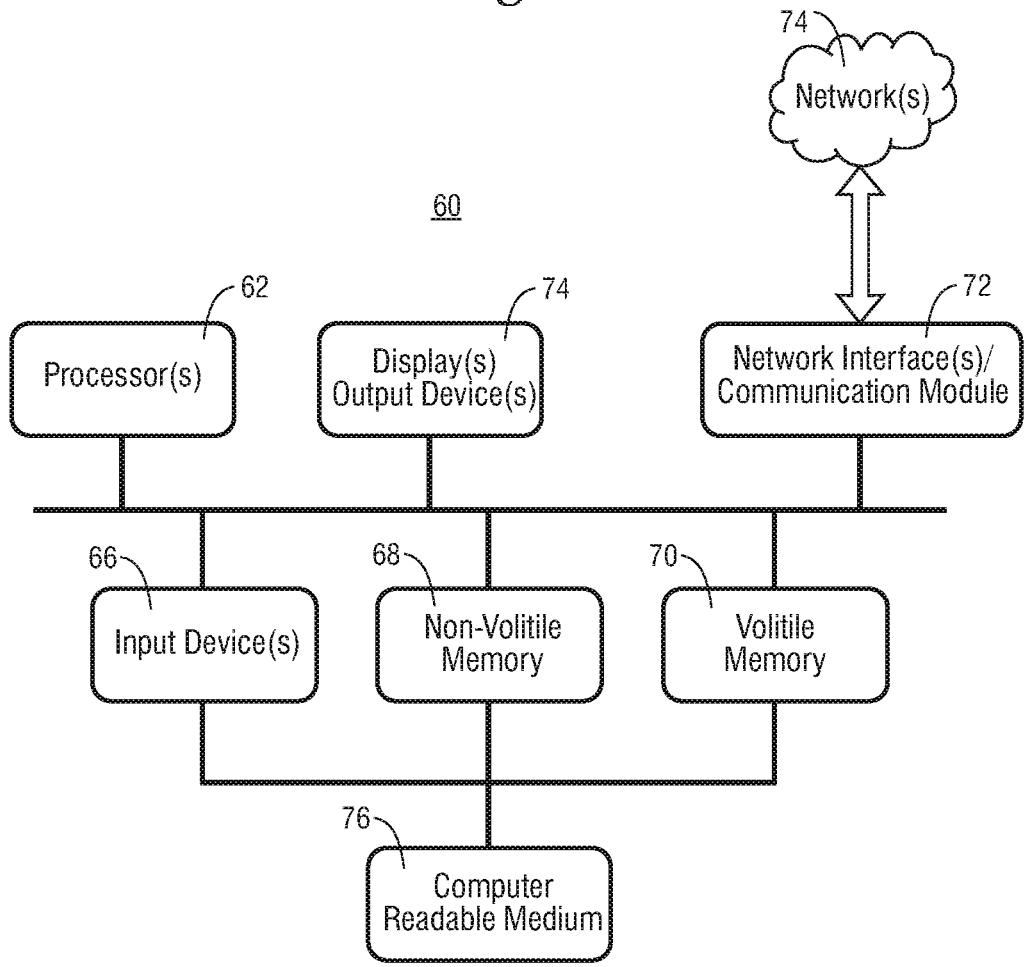
FIG. 3 is a block diagram illustrates an exemplary computing device.

Turning now to FIG. 3, a block diagram illustrates an exemplary computing device 60, through which embodiments of the disclosure can be implemented. The computing device 60 described herein is but one example of a suitable computing device and does not suggest any limitation on the scope of any embodiments presented. Nothing illustrated or described with respect to the computing device 60 should be interpreted as being required or as creating any type of dependency with respect to any element or plurality of elements. In various embodiments, a computing device 60 may include, but need not be limited to, a desktop, laptop, server, client, tablet, smartphone, or any other type of device that can compress data. In an embodiment, the computing device 60 includes at least one processor 62 and memory (non-volatile memory 68 and/or volatile memory 70). The computing device 60 can include one or more displays and/or output devices 64 such as monitors, speakers, headphones, projectors, wearable-displays, holographic displays, and/or printers, for example. Output devices 64 may further include, for example, devices that emit energy (radio, microwave, infrared, visible light, ultraviolet, x-ray and gamma ray), electronic output devices (Wi-Fi, radar, laser, etc.), audio (of any frequency), etc.

The computing device 60 may further include one or more input devices 66 which can include, by way of example, any type of mouse, keyboard, disk/media drive, memory stick/thumb-drive, memory card, pen, touch-input device, biometric scanner, voice/auditory input device, motion-detector, camera, scale, and the like. Input devices 66 may further include cameras (with or without audio recording), such as digital and/or analog cameras, still cameras, video cameras, thermal imaging cameras, infrared cameras, cameras with a charge-couple display, night-vision cameras, three-dimensional cameras, webcams, audio recorders, and the like.

The computing device 60 typically includes non-volatile memory 68 (ROM, flash memory, etc.), volatile memory 70 (RAM, etc.), or a combination thereof. A network interface 72 can facilitate communications over a network 74 via wires, via a wide area network, via a local area network, via a personal area network, via a cellular network, via a satellite network, etc. Suitable local area networks may include wired Ethernet and/or wireless technologies such as, for example, wireless fidelity (Wi-Fi). Suitable personal area networks may include wireless technologies such as, for example, IrDA, Bluetooth, Wireless USB, Z-Wave, ZigBee, and/or other near field communication protocols. Suitable personal area networks may similarly include wired computer buses such as, for example, USB and FireWire. Suitable cellular networks include, but are not limited to, technologies such as LTE, WiMAX, UMTS, CDMA, and GSM. Network interface 72 can be communicatively coupled to any device capable of transmitting and/or receiving data via one or more network(s) 74. Accordingly, the network interface hardware 72 can include a communication transceiver for sending and/or receiving any wired or wireless communication.

For example, the network interface hardware 72 may include an antenna, a modem, LAN port, Wi-Fi card, WiMax card, mobile communications hardware, near-field communication hardware, satellite communication hardware and/or any wired or wireless hardware for communicating with other networks and/or devices. One or more databases 78 may be accessed via the network(s) to remotely access data and store data.

A computer-readable medium 76 may comprise a plurality of computer readable mediums, each of which may be either a computer readable storage medium or a computer readable signal medium. A computer readable storage medium may reside, for example, within an input device 66, non-volatile memory 68, volatile memory 70, or any combination thereof. A computer readable storage medium can include tangible media that is able to store instructions associated with, or used by, a device or system. A computer readable storage medium includes, by way of example: RAM, ROM, cache, fiber optics, EPROM/Flash memory, CD/DVD/BD-ROM, hard disk drives, solid-state storage, optical or magnetic storage devices, diskettes, electrical connections having a wire, or any combination thereof. A computer readable storage medium may also include, for example, a system or device that is of a magnetic, optical, semiconductor, or electronic type. Computer readable storage media and computer readable signal media are mutually exclusive.

A computer readable signal medium can include any type of computer readable medium that is not a computer readable storage medium and may include, for example, propagated signals taking any number of forms such as optical, electromagnetic, or a combination thereof. A computer readable signal medium may include propagated data signals containing computer readable code, for example, within a carrier wave. Computer readable storage media and computer readable signal media are mutually exclusive.

The computing device 60 may include one or more network interfaces 72 to facilitate communication with one or more remote devices, which may include, for example, client and/or server devices. A network interface 72 may also be described as a communications module, as these terms may be used interchangeably.

This invention has been described with reference to several preferred embodiments. Many modifications and alterations will occur to others upon reading and understanding the preceding specification. It is intended that the invention be construed as including all such alterations and modifications in so far as they come within the scope of the appended claims or the equivalents of these claims.

The invention claimed is:

1. A method for documenting medical directives of a patient comprising:
    identifying the possible paths required to document the medical directives of the patient, wherein each path represents a possible medical situation in which a medical provider requires instructions regarding the treatment choices of the patient;
    for each path, identifying missing information and required user input to complete the path;
    generating a workflow process for a selected path that comprises collection of missing information and identification and generation of required documentation necessary for the completion of the selected path;
    executing the workflow process for the selected path;
    manipulating user provided data to generate a script comprising the instruction for a medical provider, which adhere to the legal requirements for such instruction, based on the workflow process of the selected path;
    prompting the patient to read the script and recording the patient reading the script on video;
    creating a video that combines the video recording of the patient reading from the script with a timed scrolled visual match up of the script; and
    memorializing the execution of the workflow process by creating a token to be kept on the patient's person that allows a medical provider to access the video and the medical directives of the patient to receive instruction regarding the patient's treatment choices for a given medical situation.

2. The method of claim 1 further comprising the token is embedded in or encoded on one of an identification card, a necklace, a bracelet, jewelry, a smart watch, a software application, and a device.

3. The method of claim 1 further comprising providing the user with documentation and education for each possible path.

4. The method of claim 1 in which the medical directives of a patient comprise advanced care planning, resuscitation choices, end-of-life wishes, and consent for treatment.

5. A system for documenting medical directives of a patient comprising:
    a memory;
    a processor coupled to said memory, said processor configured to:
        display a listing of possible paths required to document necessary to said medical directives of the patient wherein each path represents a possible medical situation in which a medical provider requires instruction regarding the treatment choices of the patient;
        generate a workflow process for a selected path that comprises collection of missing information and identification and generation of required documentation necessary for the completion of said selected path;
        display for said selected path missing information and required user input to complete said selected path;
        execute said workflow process;
        collect missing information and user input from the patient;
        manipulate user provided data to generate a script comprising the instruction for a medical provider, which adhere to the legal requirements for such instruction, based on the workflow process of the selected path;
        prompt the patient to read the script and record the patient reading the script on video;
        create a video recording that combines the patient reading from the script with a timed scrolled visual match up of the script following the patient's recitation of the script;
        memorialize the execution of the workflow process by creating a token to be kept on the patient's person that allows a medical provider to access the video and the medical directives of the patient to receive instruction regarding the patient's treatment choices for a given medical situation.

6. The system of claim 5 in which said medical directives of a patient comprise advanced care planning, resuscitation choices, end-of-life wishes, and consent for treatment.

7. The system of claim 5 further comprising said token is embedded in or encoded on one of an identification card, a necklace, a bracelet, jewelry, a smart watch, a software application, or a device.

8. The system of claim 5 further comprising said processer is configured to provide the user with documentation and education for each said possible path.

* * * * *